US007359520B2

(12) United States Patent
Brennan et al.

(10) Patent No.: US 7,359,520 B2

(45) Date of Patent: Apr. 15, 2008

(54) DIRECTIONAL AUDIO SIGNAL PROCESSING USING AN OVERSAMPLED FILTERBANK

(75) Inventors: Robert L. Brennan, Kitchener (CA); Edward Chau, Waterloo (CA); Hamid Sheikhzadeh Nadjar, Waterloo (CA); Todd Schneider, Waterloo (CA)

(73) Assignee: DSPFactory Ltd., Waterloo, Ontrio (CA)

(*) Notice: Subject to any disclaimer, the term of this patent is extended or adjusted under 35 U.S.C. 154(b) by 903 days.

(21) Appl. No.: 10/214,350

(22) Filed: Aug. 7, 2002

(65) Prior Publication Data

US 2003/0063759 A1 Apr. 3, 2003

(30) Foreign Application Priority Data

Aug. 8, 2001 (CA) .................................... 2354858

(51) Int. Cl.
*H04R 3/00* (2006.01)
*H04B 15/00* (2006.01)
*A61F 11/06* (2006.01)

(52) U.S. Cl. ...................... 381/92; 381/94.1; 381/94.7; 381/122; 381/71.6

(58) Field of Classification Search .................. 381/92, 381/94.7, 94.1, 122, 71.6, 94.2
See application file for complete search history.

(56) References Cited

U.S. PATENT DOCUMENTS 4,599,743 A 7/1986 Reed
4,852,123 A 7/1989 Bickley et al.
5,222,144 A 6/1993 Whikehart
5,715,319 A * 2/1998 Chu ............................ 381/26
6,236,731 B1 5/2001 Brennan et al.
6,240,192 B1 5/2001 Brennan et al.

FOREIGN PATENT DOCUMENTS

CA 2354755 2/2003
CA 2354808 2/2003

OTHER PUBLICATIONS

Claude Marro et al. "Analysis of Noise Reduction and Dereverberation Techniques Based on Microphone Arrays with Postfiltering". May 1998; pp. 240-259; vol. 6, No. 3. IEEE Transactions on Speech and Audio Processing.*

E.D. McKinney et al. "A Two-microphone Adaptive Broadband Array for Hearing Aids" May 1996. IEEE.*

Robert Brennan et al. "A Flexible Filterbank Structure For Extensive Signal Manipulations in Digital Hearing Aids". 1998.*

(Continued)

*Primary Examiner*—Vivian Chin
*Assistant Examiner*—Devona E. Faulk
(74) *Attorney, Agent, or Firm*—Daniel J. Santos

(57) ABSTRACT

A directional signal processing system for beamforming information signals. The system includes an oversampled filterbank, which has an analysis filterbank for transforming the information signals in time domain into channel signals in transform domain, a synthesis filterbank and a signal processor. The signal processor processes the outputs of the analysis filterbank for beamforming the information signals. The synthesis filterbank transforms the outputs of the signal processor to a single information signal in time domain.

21 Claims, 5 Drawing Sheets

OTHER PUBLICATIONS

Bicevskis, Robert; "Complex-Valued Phase-Locked Loops"; Thesis; Sep. 1986; Department of Electrical Engineering, University of Toronto; Toronto, Canada.
Crawford, James A.; "Frequency Synthesizer Design Handbook"; Book; 1994; pp. 308-343; Artech House, Inc.; 685 Canton Street, Norwood, MA 02062, USA; ISBN 0-89006-440-7.
Meyer, Robert G. et al.; "Blocking and Desensitization in RF Amplifiers"; Journal; Aug. 1995; pp. 944-946; vol. 30, Issue 8; IEEE Journal of Solid-State Circuits; USA.
Abidi, Asad A.; "Direct-Conversion Radio Transceivers for Digital Communications"; Journal; Dec. 1995; pp. 1399-1410; vol. 30, Issue 12; IEEE Journal of Solid-State Circuits; USA.
Song, Bang-Sup et al.; "A Digital FM Demodulator for FM, TV, and Wireless"; Journal; Dec. 1995; pp. 821-825; vol. 42, Issue 12; IEEE Transactions on Circuits and Systems-II: Analog and Digital Signal Processing; USA.
Park, Jaejin; "A 5-MHz IF Digital FM Demodulator"; Journal; Jan. 1999; pp. 3-11; vol. 34, Issue 1; IEEE Journal of Solid-State Circuits; USA.
U.S. Appl. No. 10/214,057, filed Jun. 12, 2003, Brennan et al.
Claude Marro, Yannick Mahieux, and K. Uwe Simmer; "Analysis of Noise Reduction and Dereverberation Techniques Based on Microphone Arrays With Postfiltering"; Article; May 1998; pp. 240-259; vol. 6, No. 3; IEEE Transactions on Speech and Audio Processing.
Bernard Widrow; "A Microphone Array for Hearing Aids"; Article; pp. 1-5; Stanford University, USA.
Julie Elise Greenberg; "Improved Design of Microphone-Array Hearing Aids"; Thesis; Aug. 31, 1994; Harvard-MIT Division of Health Sciences and Technology; USA.
Robert Brennan and Todd Schneider; "A Flexible Filterbank Structure for Extensive Signal Manipulations in Digital Hearing Aids"; Article; 1998; IEEE; Dspfactory, Waterloo, Ontario, Canada, N2V 1K8.
Edward Yu-Ho Chau; " Adaptive Noise Reduction Using a Cascaded Hybrid Neural Network"; Thesis; Jun. 2001; Presented to The Faculty of Graduate Studies of The University of Guelph.
Sheikhzadeh, Hamed et al; "Real-Time Speech Synthesis on an Ultra Low-Resource, Programmable DSP System"; Article submitted to IEEE for possible publication; 4 total pages.

* cited by examiner

DIRECTIONAL AUDIO SIGNAL PROCESSING USING AN OVERSAMPLED FILTERBANK

CROSS-REFERENCE TO RELATED APPLICATION

This application claims priority to copending Canadian Patent Application entitled, "Directional Audio Signal Processing Using an Oversampled Filterbank," having Ser. No. 2,354,858, filed Aug. 8, 2001, which is entirely incorporated herein by reference.

FIELD OF THE INVENTION

The present invention relates to audio signal processing applications where the direction of arrival of the audio signal(s) is the primary parameter for signal processing. The invention can be used in any application that requires the input audio signal(s) to be processed based on the spatial direction from which the signal arrives.

Application of this invention includes, but is not limited to, audio surveillance systems, hearing aids, voice-command systems, portable communication devices, speech recognition/transcription systems and any application where it is desirable to process signal(s) based on the direction of arrival.

BACKGROUND OF THE INVENTION

Directional processing can be used to solve a multitude of audio signal processing problems. In hearing aid applications, for example directional processing can be used to reduce the environmental noise that originates from spatial directions different from the desired speech or sound, thereby improving the listening comfort and speech perception of the hearing aid user. In audio surveillance, voice-command and portable communication systems, directional processing can be used to enhance the reception of sound originating from a specific direction, thereby enabling these systems to focus on the desired sound. In other systems, directional processing can be used to reject interfering signal(s) originating from specific direction(s), while maintaining the perception of signal(s) originating from all other directions, thereby insulating the systems from the detrimental effect of interfering signal(s). Beamforming is the term used to describe a technique which uses a mathematical model to maximise the directionality of an input device. In such a technique filtering weights may be adjusted in real time or adapted to react to changes in the environment of either the user or the signal source, or both.

Traditionally, directional processing for audio signals has been implemented in the time-domain using Finite Impulse Response (FIR) filters and/or simple time-delay elements. For applications dealing with simple narrow band signals, these approaches are generally sufficient. To deal with complex broadband signals such as speech, however, these time-domain approaches generally provide poor performance unless significant extra resources, such as large microphone arrays, lengthy filters, complex post-filtering, and high processing power are committed to the application. Examples of these technologies are described in "Analysis of Noise Reduction and Dereverberation Techniques Based on Microphone Arrays with Postfiltering", C. Marro, Y. Mahieux and K. U. Simmer, *IEEE Trans. Speech and Audio Processing*, vol. 6, no. 3. 1998, and in "A Microphone Array for Hearing Aids". B. Widrow, *IEEE Adaptive Systems for Signal Processing, Communications and Control Symposium*, pp. 7-11, 2000.

In any directional processing algorithm, an array of two or more sensors is required. For audio directional processing, either omni-directional or directional microphones are used as the sensors. FIG. 1 shows a high-level block diagram of a general directional processing system. As seen in the figure, while there are two or more inputs 100, 105 to the system 110, there is generally only one output 120.

There are two common types of directional processing algorithms adaptive beamforming and fixed beamforming. In fixed beamforming, the spatial response—or beampattern—of the algorithm does not change with time, as opposed to a time varying beampattern in adaptive beamforming. A beampattern is a polar graph that illustrates the gain response of the beamforming system at a particular signal frequency over different directions of arrival. FIG. 2 shows an example of two different beampatterns in which signals from certain directions of arrival are attenuated (or enhanced) relative to signals from other directions. The first is the cardioid pattern 200, typical of some end-fire microphone arrays, and the other 205 is the beampattern typical of broad-side microphone arrays. FIG. 3 illustrates typical configurations for end-fire 300, 305, 310 and broadside 320, 325, 330 microphone arrays.

More recent Fast Fourier Transform (FFT)-based approaches attempt to improve upon the traditional time-domain approaches by implementing directional processing in the frequency-domain. However, many of these FFT-based approaches suffer from wide sub-bands that are highly overlapped, and therefore provide poor frequency resolution. They also require longer group delays and more processing power in computing the FFT.

Accordingly, there is a need to solve the problems noted above and also a need for an innovative approach to enhance and/or replace the current technologies.

SUMMARY OF THE INVENTION

The invention described herein is applicable to both the end-fire and broadside microphone configurations in solving the problems found in conventional beamforming solutions. It is also possible to apply the invention to other geometric configurations of the microphone array, as the underlying processing architecture is flexible enough to accommodate a wide range of array configurations. For example, more complex directional systems based on two or three-dimensional arrays, used to produce beampatterns having three dimensions, are known and are suitable for used with this invention.

In accordance with an aspect of the present invention, there is provided a directional signal processing system for beamforming a plurality of information signals, which includes: a plurality of microphones; an oversampled filterbank comprising at least one analysis filterbank for transforming a plurality of information signals in time domain from the microphones into a plurality of channel signals in transform domain, and one synthesis filterbank; and a signal processor for processing the outputs of said analysis filterbank for beamforming said information signals. The synthesis filterbank transforming the outputs of said signal processor to a single information signal in time domain.

In accordance with a further aspect of the present invention, there is provided a method of processing a plurality of channel signals for achieving approximately linear phase response within the channel, which includes a step of performing filtering by applying more than one filter to at least one channel signal.

In accordance with a further aspect of the present invention, there is provided a method of processing at least one information signal in time domain for achieving approximately linear phase response, which includes a step of performing an oversampling using at least one oversampled analysis filterbank. The oversampled analysis filterbank applies at lease one fractional delay impulse response to at least one filterbank prototype window time.

The directional processing system of the invention takes advantage of oversampled analysis/synthesis filterbanks to transform the input audio signals in time domain to a transform domain. Example of common transformation methods includes GDFT (Generalized Discrete Fourier Transform), FFT, DCT (Discrete Cosine Transform), Wavelet Transform and other generalized transforms. The emphasis of the invention described herein is on a directional processing system employing oversampled filterbanks, with the FFT method being one possible embodiment of said filterbanks. An example of the oversampled, FFT-based filterbanks is described in U.S. Pat. No. 6,236,731 "Filterbank Structure and Method for Filtering and Separating an Information Signal into Different Bands. Particularly for Audio Signal in Hearing Aids" by R. Brennan and T. Schneider, incorporated herein by reference. An example of an hearing aid apparatus employing said oversampled filterbanks is described in U.S. Pat. No. 6,240,192 "Apparatus for and Method for Filtering in an Digital Hearing Aid. Including an Application Specific Integrated Circuit and a Programmable Digital Signal Processor" by R. Brennan and T. Schneider, incorporated herein by reference. However, this use of oversampled analysis/synthesis filterbanks in the general framework of the directional processing system disclosed herein has not been reported before.

The sub-band signal processing approach described henceforth, with its corresponding FFT-based method being one possible embodiment of the oversampled filterbanks employed in the invention disclosed herein, has the advantage of directly addressing the frequency-dependent characteristics in the directional processing of broadband signals. Compared to traditional time-domain and FFT-based approaches, the advantages of using an oversampled filterbank in sub-band signal processing according to the present invention are as follows:

1) Equal or greater signal processing capability at a fraction of the processing power, 2) Orthogonalization effect of the subband signals in the different frequency bins due to the FFT of the oversampled filterbank, 3) Improved high frequency resolution, 4) Better spatial filtering, 5) Wide range of gain adjustment at a very low cost of processing power, and 6) Ease of integration with other algorithms.

As a result, the sub-band directional processing approach with an oversampled filterbank allows powerful directional processing capability to be implemented on miniature low-power devices. For applications employing the invention, this means:

1) Better listening comfort and speech perception (particularly important for hearing aids), 2) More accurate recognition for speech and speaker recognition systems, 3) Better directionality and higher SNR, 4) Low group delay, and 5) Lower power consumption.

Thus, the present invention is applicable for audio applications that require a high fidelity and ultra low-power processing platform.

A further understanding of the other features, aspects, and advantages of the present invention will be realized by reference to the following description, appended claims, and accompanying drawings.

BRIEF DESCRIPTION OF THE DRAWINGS

Embodiments of the invention will now be described with reference to the accompanying drawings, in which.

DETAILED DESCRIPTION OF THE INVENTION

Figure 1:
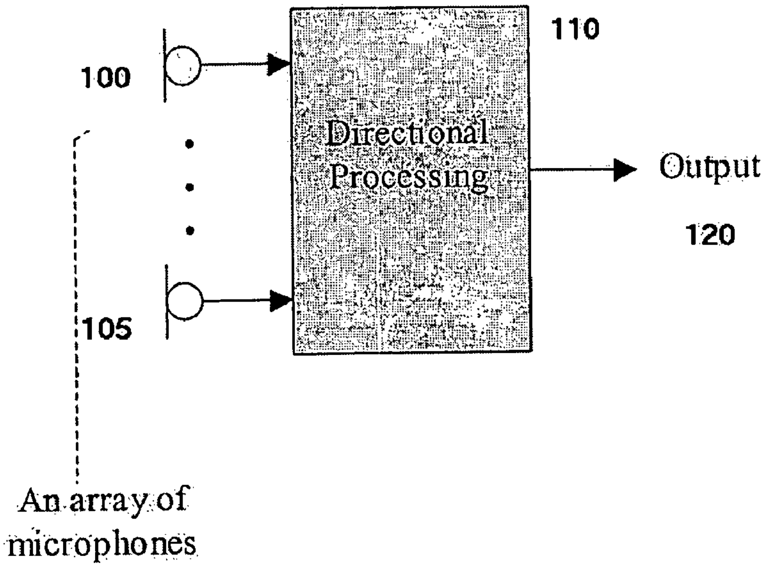
FIG. 1 (prior art)
FIG. 1 shows a block diagram of a general directional processing system.
Figure 2:
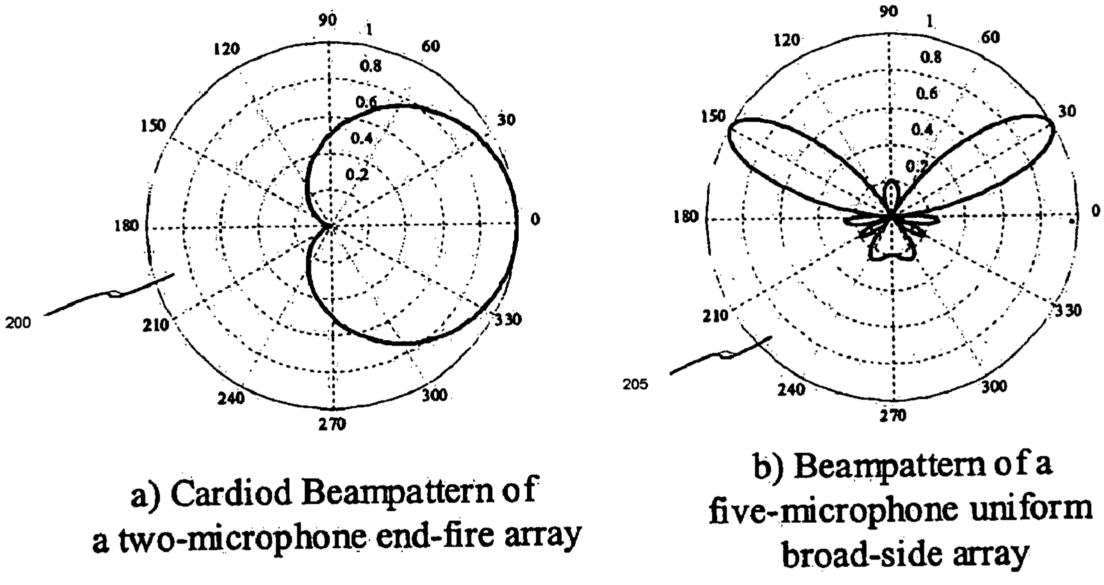
FIG. 2 (prior art)
FIG. 2 shows an example of two different beampatterns.
Figure 3:
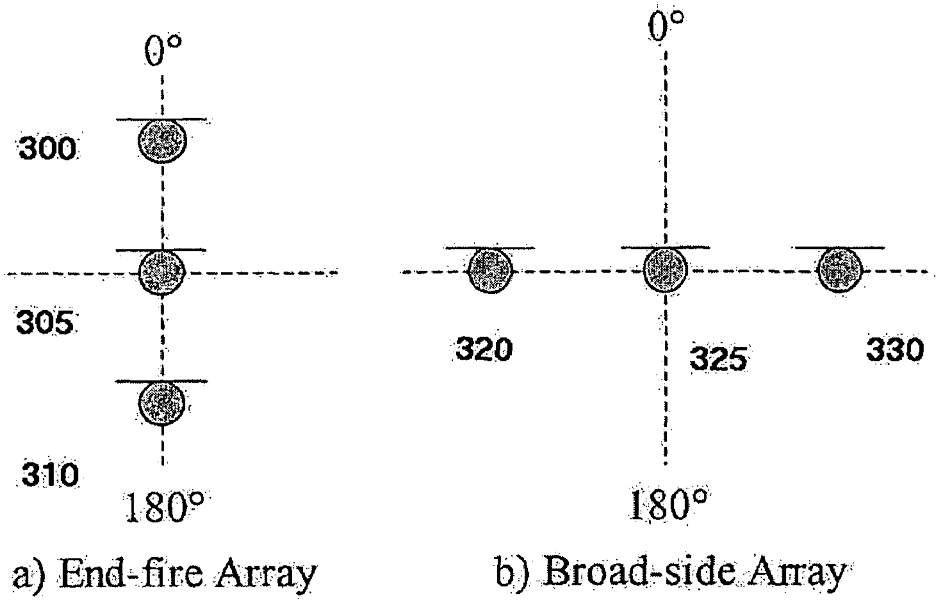
FIG. 3 (prior art)
FIG. 3 shows the array configuration of the end-fire and broadside arrays.
Figure 4:
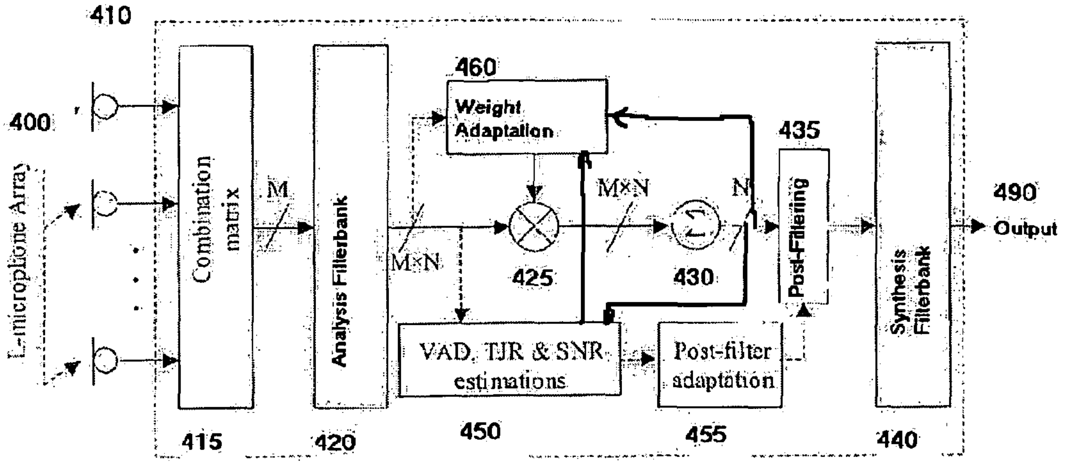
FIG. 4 shows a block diagram of the adaptive beamformer system according to one embodiment of the invention.

Turning now to FIG. 4 an adaptive beamformer system embodying the invention in block diagram form is shown. Note that it is assumed that the outputs of the L microphones 400 ($L \geqq 2$) are already converted to digital form by a set of analogue-to-digital converters (ADC) (not shown). Similarly, the output is assumed to be converted from digital form by an digital-to-analogue converter (DAC) (not shown) to produce an appropriate output signal 490. The digitized outputs of the L microphones 400 are first combined in a combination matrix 415. The combination matrix 415 can be any Finite Impulse Response (FIR) filter with multiple input and outputs (the number of outputs M being less or equal to the number of inputs L ($M \leqq L$)). Suitable matrices include a delay-and-sum network, a sigma-delta network, and a one-to-one mapping of the inputs to the outputs (for example some general matrix through which L inputs are transformed into L (i.e. M=L) outputs)). The M outputs of the combination matrix 415 are then transformed to the frequency domain by an analysis filterbank 420, with N sub-bands per combination matrix output to produce M×N signals for processing. The (oversampled) analysis filterbank 420 used in this embodiment is the weighted-overlap-add (WOLA) filterbank described in U.S. Pat. No. 6,236,731 "Filterbank Structure and Method for Filtering and Separating an Information Signal into Different Bands. Particularly for Audio Signal in Hearing Aids" by R. Brennan and T. Schneider. An adaptive system 460 then generates a weighted sum of the analysis filterbank outputs which are applied to the outputs by the multiplier 425. The weights (also known as filter taps) of the adaptive system 460 are adapted according to well known adaptive strategies including, but not limited to, those based on Least Mean Squares (LMS), and Recursive Least Squares (RLS). The outputs of the multiplier 425 are then passed to a summer 430 which produces N outputs, each a weighted sub-band derived from the original microphone signals. The overall adaptation process is further controlled by the outputs of a side process comprising an estimations block 450, and a post-filter adapter 455. The estimations block of the side process 450 may include one or more of a Voice Activity Detector (VAD), a Target-to-Jammer Ratio (TJR) estimator, and a Signal-to-Noise Ratio (SNR) estimator. The outputs of the estimations block 450 are then used to slow down, speed up, or inhibit the adaptation process by controlling the weight adaptation 460, and also combined with post-filter adaptation 455 to control the post-filter 435. After passing through a summer 430 which combines the processed M×N inputs received from the adaptive processor 460, 425 into N a sub-bands, the post-filter 435 operates in the frequency domain to further process the signal depending on the output from the post-filter adapter 455. After post-filtering the N sub-band frequency domain outputs ate processed by a synthesis filterbank 440 to generate a time-domain output 490.

Oversampled filterbanks offer the general advantages explained in the summary above by virtue of their flexibility and the fabrication technology. Further advantages of their use for the adaptive beamformer application of the present invention are:

1) Directional processing using prior art techniques requires very long adaptive filter lengths particularly in reverberant environments, as reported by other researchers (see J. E. Greenberg, "Improved Design of Microphone-Array Hearing Aids". *Ph.D Thesis*, MIT. September 1994). The sub-band adaptation using the oversampled filterbank can efficiently implement the equivalent of a long filter through parallel sub-band processing.

2) In frequency domain beamforming (both adaptive and fixed), there is a need to weight the Fast Fourier Transform (FFT) coefficients in a highly unconstrained way. A typical adaptive post-filtering operation is the multiple-microphone Wiener filtering, in which the frequency response is adapted depending on the Signal-to-Noise Ratio (SNR) of the received signal. In this process, there is a need for unconstrained gain adjustments across the frequency bands. The oversampled filterbank implementation allows a wide range of gain adjustments without creating the so-called "time-aliasing" problem that happens in the critically sampled filterbanks. It has been observed that the operation cost is not much higher than the critically sampled filterbanks and much lower than the undecimated filterbanks. For more information see U.S. Pat. No. 6,236,731 "Filterbank Structure and Method for Filtering and Separating an Information Signal into Different Bands. Particularly for Audio Signal in Hearing Aids". R. Brennan and T. Schneider, and "A Flexible Filterbank Structure for Extensive Signal Manipulations in Digital Hearing Aids". R. Brennan and T. Schneider, *Proc. IEEE Int. Symp. Circuits and Systems*, pp. 569-572, 1998.

3) The so-called "Misadjustment" error, where there is excessive Mean Square Error when compared to an optimal Wiener filter, is typically present in adaptive systems. It is well known and understood that sub-band and orthogonal decomposition reduces this problem. The oversampled filterbank used in the invention employs such decomposition in at least one preferred embodiment.

4) Estimation of Target-to-Jammer Ratio (TJR) usually requires the cross-correlation of two or more microphone outputs (as described in "Improved Design of Microphone-Array Hearing Aids". J. E. Greenberg, *Ph.D Thesis*, MIT. September 1994). The frequency domain implementation of the process using the oversampled filterbank is much faster and more efficient than the time-domain methods previously used.

5) By using the side process outputs of the Voice Activity Detector (VAD), the Target-to-Jammer Ratio (TJR) estimator, and the Signal-to-Noise Ratio (SNR) estimator, the adaptation process can be slowed down or totally inhibited when there is a strong target (like speech) presence. This enables the system to work in reverberant environments. There are enough pauses in speech signal to ensure that the inhibition process does not disturb the system performance. A suitable efficient frequency domain VAD that uses the oversampled filterbank is described in a co-pending patent application "Sub-band Adaptive Signal Processing in an Oversampled Filterbank". K. Tam, et, al., Canadian Patent Application Serial 2,354,808. August 2001, U.S. application Ser. No. 10/214,057, incorporated herein by reference.

Figure 5:
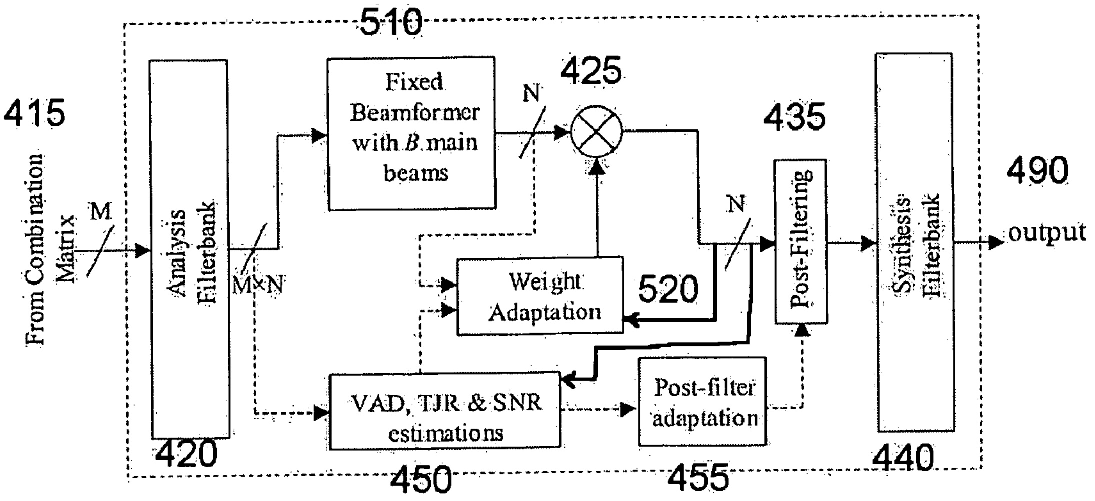
FIG. 5 shows a block diagram of the adaptive beamformer system according to another embodiment of the invention.

According to a further preferred embodiment of the invention, shown in FIG. 5, the weight adaptation process is performed on a set of B fixed beams for each sub-band constructed or synthesised from the sub-bands derived from each microphone output, rather than the microphone outputs themselves or the sub-bands of such outputs. Within FIG. 5 most of the elements are the same as FIG. 4, and have been notated with the same reference numbers. Therefore these elements will not be described again. The new elements introduced in this embodiment are the Fixed Beamformer 510 which produces B main beams from the sub-bands, and a weight adaptation block 520 which controls the multiplier 425, based on inputs from the VAD, TJR and SNR estimations block 450, and the sub-band signals output by the Fixed Beamformer 510. Generally this strategy provides a smoother and more robust transition when the adaptive filtering weights are changed. The weight adaptation is controlled by some TJR and/or SNR estimations based on, but not limited to, one or more of the following signal statistics: auto-correlation, cross-correlation, subband magnitude level, subband power level, cross-power spectrum, cross-power phase, cross-spectral density, etc. One possible filtering weight adaptation strategy based on a simplified SNR estimation is proposed here, and other similar or related methods may occur to those skilled in the art, and it is our intention that these be covered. When the side process detects the absence (or near absence) of the target, the time averaged energy of the noise in each of the beams (denoted by En(I), I=1, 2, . . . , B) is measured. When the target reappears, the time-averaged energy of the target (Et(I)) and the SNR in each beam (SNR(I)) are estimated, given the total averaged energy in the beam Etot(J), by:

$$Et(I)=Etot(I)-\mathrm{En}(I),\ I=1, 2, \ldots, B$$

$$SNR(I)=Et(I)/En(I)$$

If the noise statistics, and noise and target directions do not change much from one target signal pause to the next pause, the SNR(I) for each beam can be used to make a weighted sum of the beams. However, if the noise is highly non-stationary, or if the noise and/or target sources are moving quickly, an adaptive processor should be employed to adjust the weights. For improved performance, the fixed beamformer can be designed with a set of narrow beams covering the azimuth and elevation angles of interest for a particular application.

A further embodiment of the invention in a fixed beamforming application will now be discussed. The classical method of implementing a fixed beamformer is the delay-and-sum method. Because of the physical spacing of the microphones in the array, there is an inherent time delay between the signals received at each microphone. Hence, the delay-and-sum method utilizes a simple time-delay element to properly align the received signals so that the signals arriving from certain directions can be maximally in-phase, and contribute coherently to the summed output signal. And signal arriving from other directions then contributes incoherently to the output signal, so that its signal power can be reduced at the output.

Figure 6:
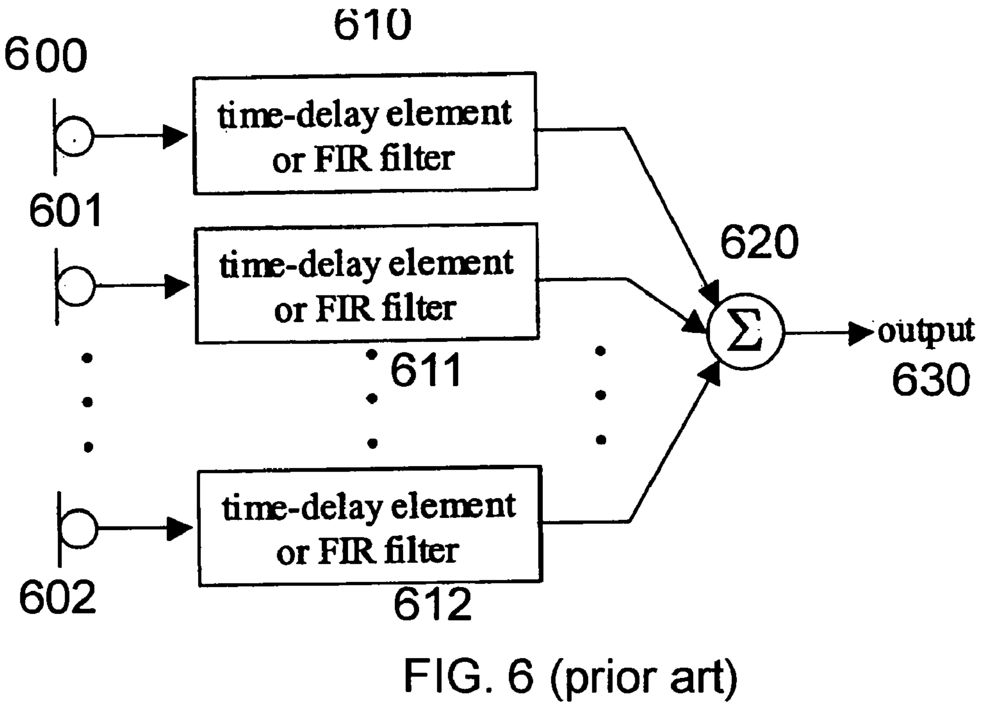
FIG. 6 (prior art)
FIG. 6 shows a traditional time-domain beamformer structure.

With the FIR-filter method, the FIR filters are generally designed so that their phase responses take on the role of aligning the received signals to create the desired beampattern. These filters can be designed using transformation from analogue filters, or direct FIR filter design approaches. When complex broadband signals are involved, such time-domain filter designs generally require the availability of a significant amount of computation power. For comparison, FIG. 6 shows a fixed beamformer structure using the prior art time-domain approach. In the figure an array of three microphones 600, 601, 602 is disposed in a known pattern, although a greater number of microphones might also be used. The outputs of each microphone in the array 600, 601, 602 is passed to a separate time-delay element (or FIR Filter) 610, 611, 612, whose outputs are passed in turn to a summer 620. The summer 620, when the time delay elements are correctly set as described above, provides an enhanced output 630 for a particular spatial direction with respect to the microphone array. Usually, this setting of the time delay elements 610, 611, 612, is accomplished dynamically, but is often a compromise depending on the factors including the frequency of the signal, and the relative spacing of the microphones in the array. If a number of beams were required, each would be constructed or synthesised using a similar circuit. For that reason these systems are expensive, high in power consumption, complex and hence limited in application.

Figure 7:
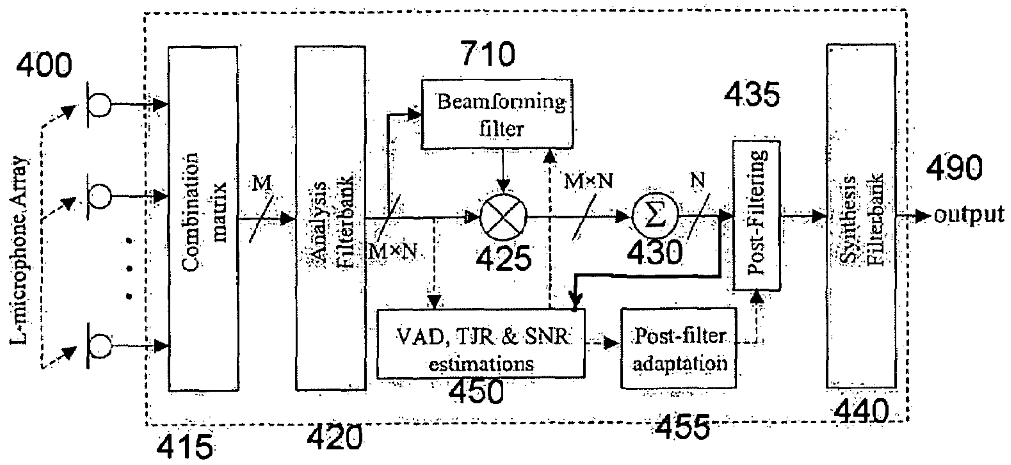
FIG. 7 shows a sub-band beamformer using an oversampled filterbank according to another embodiment of the present invention.

Further preferred embodiments of the invention described herein perform a series of narrowband processing steps to solve the more complex broadband problem. The use of the oversampled filterbank allows the narrowband processing to be done in an efficient and practical manner. FIG. 7 shows a sub-band fixed beamformer using an oversampled filterbank according to another embodiment of the present invention. The system is very similar to that described in FIG. 4. For convenience and clarity, the same components are identified by the same reference numbers in both figures. The digital versions of the signals received at the L-microphone array 400 are combined through a combination matrix 415 into M signal channels ($M \leqq L$) before being sent to the analysis filterbank 420. The analysis filterbank 420 generates N frequency sub-bands for each channel, whereupon the beamforming filter 710 applies complex-valued gain factors for achieving the desired beampattern, based on inputs from the VAD, TJR and SNR estimation block 450, and the level of signal in the sub-bands produced by the analysis filterbank 420. The gain factors can be applied either independently for each channel and sub-band, or jointly through all channels and/or sub-bands by some matrix operation. After the gain factors are applied by the multiplier 425, the M channels are combined to form a single channel through a summation operation 430. A post-filtering process 435 can then be applied to provide further enhancement as before (such as improving the SNR) making use of the side process 450, 455. Afterwards, the synthesis filterbank 440 transforms the single channel composed of N sub-bands back to time-domain. In further embodiments, the post-filtering is applied in the time-domain, after the signal channel is converted back to time-domain by the synthesis filterbank, although, compared to frequency-domain post-filtering, this typically requires more processing power.

Figure 8:
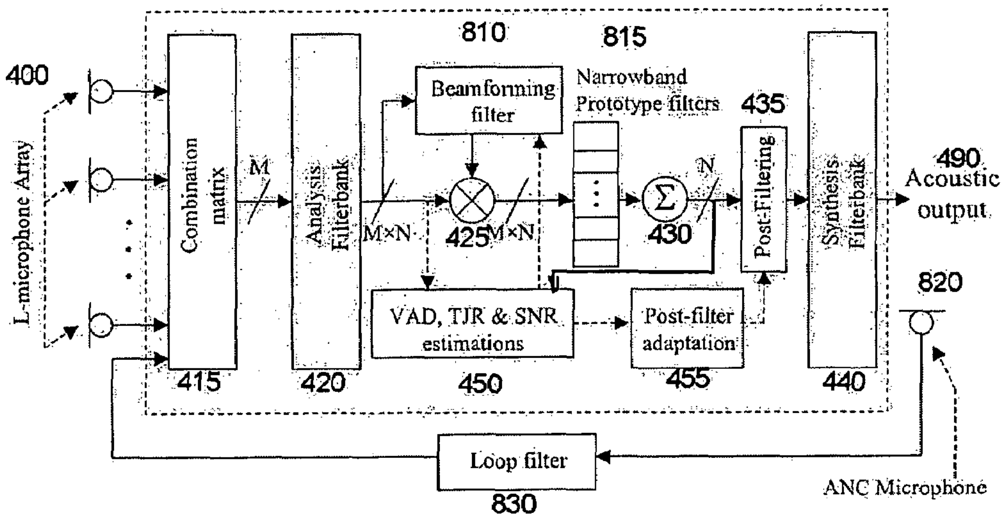
FIG. 8 shows another preferred embodiment modified for compensating the bandwidth of the sub-bands.

The complex-valued gain factors of the beamforming filter can be derived in a number of ways. For example, if an analogue filter has been designed, then it can be implemented directly in sub-bands by simply using the centre frequency of each sub-band to look up the corresponding complex response of the analogue filter (frequency sampling). With sufficiently narrow sub-bands, this method can create a close digital equivalent of the analogue filter. In a further embodiment of the invention, to closely approximate the ideal phase and amplitude responses for wider sub-bands, a narrowband filter to each sub-band output is applied as will now be described in relation to FIG. 8 in which again, many of the components are the same as for the earlier FIG. 7, and for which those same components are for convenience and clarity referred to by the same reference numbers. The additional function for this embodiment is performed in the Narrowband Prototype Filters 815. To approximate an ideal linear phase response of the beamformer, the filters 815 are designed as all-pass with a narrowband linear phase response. In a further embodiment, the filters are further constrained to being identical, and are moved back before the FFT modulation stage by combining its impulse response with the filterbank prototype window. One possible combination is a time convolution of the filterbank prototype window with a fractional delay impulse response. As a means of eliminating the external noise at the acoustic output stage, an Active Noise Cancellation (ANC) module is optionally added to the system in a manner similar to the system described in a co-pending patent application "Sound Intelligibility Enhancement Using a Psychoacoustic Model and an Oversampled Filterbank". T. Schneider et. al., Canadian Patent Application, serial 2,354,755. U.S. Ser. No. 10/214,057, incorporated herein by reference. The ANC, as also shown in FIG. 8, consists of a microphone 820 positioned at the output 490, plus a loop filter 830 to provide feedback to the combination matrix 415.

Figure 9:
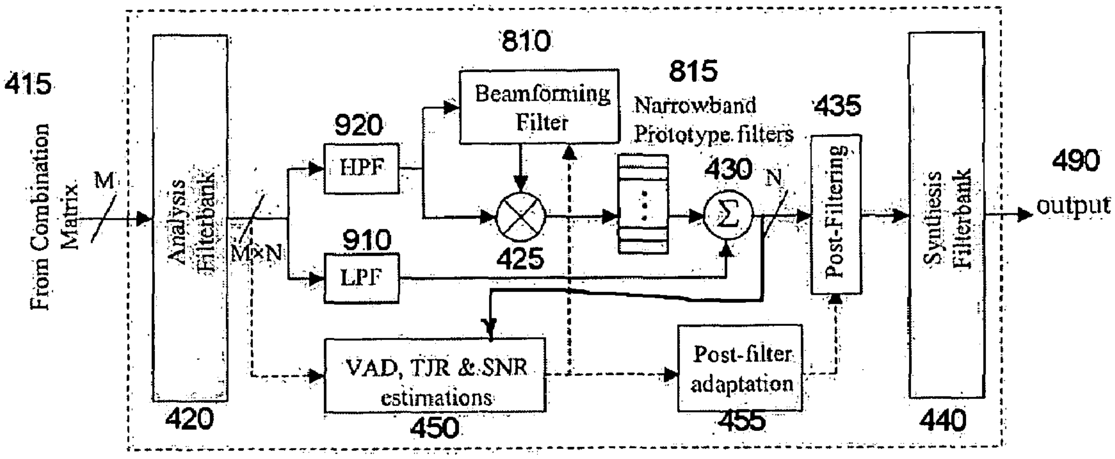
FIG. 9 shows another preferred embodiment modified for compensating the undesirable low-frequency beamformer response.

Almost all implementations of beamformers suffer from a low-frequency roll-off effect. To compensate for this effect, most systems, including the proposed system, introduce low-frequency amplification. However, because of the unavoidable microphone internal noise, this inherently leads to a high level of output noise at very low frequencies. As is well known, the result is that the desired beampattern call only be obtained for the frequencies above some cut-off value (usually around 1 kHz based on a particular microphone separation distance). In a further embodiment, shown in FIG. 9, to avoid a high-level of low-frequency noise, the microphone signals are separated into high frequency and low-frequency components by high-pass filter (HPF) 920 and low-pass filter (LPF) 910. Again, many of the same components used in the preferred embodiment described with reference to FIG. 7 are used, performing the same function, and are given the same reference numbers. The high frequency components output by the high pass filter 920 are processed by the beamforming filter 710, multiplier 7425, and Narrow band prototype filters 815, as before. The low-frequency components by-pass the beamforming filter 710, multiplier 7425, and Narrow band prototype filters 815, relying solely on the post-filter 435 to provide low-frequency signal enhancement.

Figure 10:
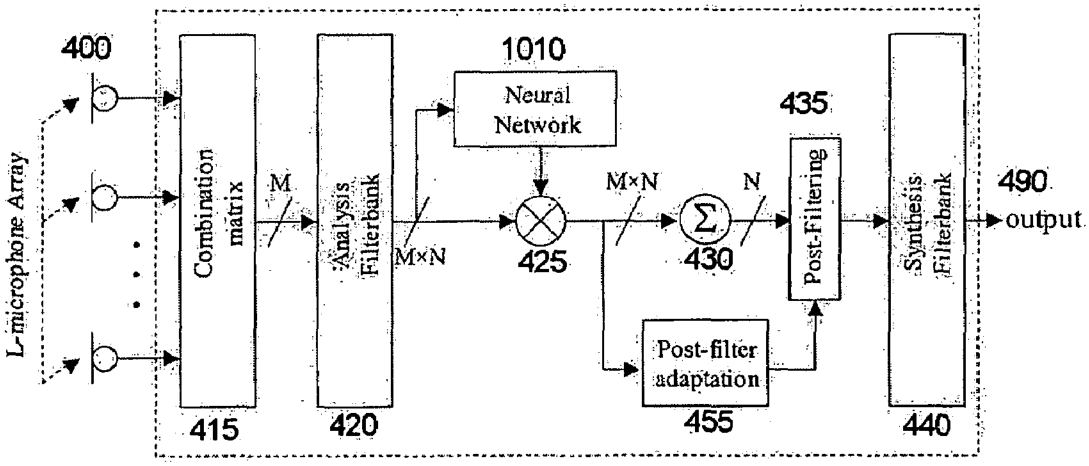
FIG. 10 show another preferred embodiment using a neural network as a beamformer filter according to the invention.

Besides the conventional digital filter design methods, the beamformer filter 710 in FIG. 7 can also be implemented using an Artificial Neural Network (ANN). The ANN can be employed as a type of non-parametric, robust adaptive filter, and has been increasingly investigated as a viable signal processing approach. One further possible embodiment of the present invention is to implement a neural network 1010 as a complete beamforming filter, as shown in FIG. 10. Once again the same reference numbers as FIG. 4 are used for those components that are unchanged in function. The neural network 1010 accepts inputs from the sub-bands output by the analysis filterbank, and uses these to control the multiplier 425 which affect those sub-bands. The post filter adaptor 455 in this case accepts as input the results of each sub-band after the multiplier operation 425, and is again used to adapt the post filtering block 435.

The Cascaded Hybrid Neural Network (CHNN), designed specifically for sub-band signal processing, can be used to implement a beamforming filter. The CHNN consists of two classical neural networks—the Self-Organising Map (SOM) and Radial Basis Function Network (RBFN)—connected in a tapped-delay line structure (for example, see "Adaptive Noise Reduction Using a Cascaded Hybrid Neural Network". E. Chau. *M. Sc. Thesis*, School of Engineering, University of Guclph, 2001. The neural network can also be used to provide integrated function, of the ANC, the beamforming filter and other signal processing algorithms in the sub-band signal processing system.

While the present invention has been described with reference to specific embodiments, the description is illustrative of the invention and is not to be construed as limiting the invention. Various modifications may occur to those skilled in the art without departing from the true spirit and scope of the invention as defined by the appended claims.

What is claimed is:

1. A directional signal processing system for beamforming a plurality of information signals, said directional signal processing system comprising:

a plurality of microphones;

an analog-to-digital convertor for converting a plurality of said information signals from said microphones to a plurality of digital information signals;

an oversampled filterbank comprising at least one analysis filterbank for transforming said digital information signals in time domain into a plurality of channel signals in transform domain, and one synthesis filterbank, said oversampled filterbank being a weighted-overlap-add (WOLA) filterbank, said channel signal being a complex-valued, demodulated time-frequency signal;

a signal processor for processing the outputs of said analysis filterbank for beamforming said information signals, said synthesis filterbank transforming the outputs of said signal processor to a single digital information signal in time domain;

a post-filter provided between said signal processor and said synthesis filterbank;

a controller for controlling said post-filter; and a digital-to-analog convertor for converting said single digital information signal to an analog information signal, and at least one of the following: a voice activity detector operably coupled to at least one of said signal processor and controller; a target-to-jammer ration estimator operably coupled to at least one of said signal processor and controller; a signal-to-noise ration estimator operably coupled to at least one of said signal processor and said controller; a combination matrix provided between said analog-to-digital converter and said analysis filterbank for pre-processing of said information signals in time domain; an active noise processor comprising a microphone and a loop filter.

2. A directional processing system as claimed in claim 1, wherein said controller controls said post-filter based on the outputs of at least one of any of the following:

said voice activity detector;

said target-to-jammer ratio estimator;

said signal-to-noise ratio estimator.

3. A directional processing system as claimed in claim 1, wherein said controller controls said post-filter based on the outputs of at least one of any of the following:

said voice activity detector;

said target-to-jammer ratio estimator;

said signal-to-noise ratio estimator.

4. A directional processing system as claimed in claim 1, wherein said combination matrix is a FIR filter.

5. A directional processing system as claimed in claim 1, wherein said combination matrix is a FIR filter.

6. A directional processing system as claimed in claim 1, wherein said combination matrix is an IIR filter.

7. A directional processing system as claimed in claim 1, wherein said combination matrix is an IIR filter.

8. A directional processing system as claimed in claim 1, wherein said signal processor comprises:

at least one multiplier for multiplying the outputs of said analysis filterbank with at least one weight factor; and at least one summation circuit for summing the outputs of said multiplier to form the channel signals.

9. A directional processing system as claimed in claim 1, wherein said signal processor further comprises:

at least one multiplier for multiplying the outputs of said analysis filterbank with at least one weight factor; and at least one summation circuit for summing the outputs of said multiplier to form the channel signals.

10. A directional processing system as claimed in claim 8, wherein said signal processor further comprises an adaptive processor for adjusting said weight factor based on a feedback adaptive processing.

11. A directional processing system as claimed in claim 9, wherein said signal processor further comprises an adaptive processor for adjusting said weight factor based on a feedback adaptive processing.

12. A directional processing system as claimed in claim 10, wherein said adaptive processor adjusts said weight factor based on the outputs of at least one of any of the following:

a voice activity detector;

a target-to-jammer ratio estimator;

a signal-to-noise ratio estimator.

13. A directional processing system as claimed in claim 11, wherein said adaptive processor adjusts said weight factor based on the outputs of at least one of any of the following:

said voice activity detector;

said target-to-jammer ratio estimator;

said signal-to-noise ratio estimator.

14. A directional processing system as claimed in claim 1, wherein said signal processor comprises a module for maintaining a linear phase response for filtering the complex-valued, demodulated time-frequency signal.

15. A directional signal processing system for beamforming a plurality of information signals, said directional signal processing system comprising:

a plurality of microphones;

an analog-to-digital convertor for converting said information signals from said microphones to a plurality of digital information signals;

an oversampled filterbank comprising at least one analysis filterbank for transforming said digital information signals in time domain into a plurality of channel signals in transform domain, and one synthesis filterbank;

a signal processor for processing the outputs of said analysis filterbank for beamforming said information signals, said synthesis filterbank transforming the outputs of said signal processor to a single digital information signal in time domain;

a post-filter provided between said signal processor and said synthesis filterbank;

a controller for controlling said post-filter;

a digital-to-analog convertor for converting said single digital information signal to an analog information signal; and at least one of the following:

a voice activity detector;

a target-to-jammer ratio estimator;

a signal-to-noise ratio estimator;

a combination matrix provided between said analog-to-digital convertor and said analysis filterbank for pre-processing of said information signals in time domain; and an active noise processor comprising a microphone and a loop filter, wherein said controller controls said post-filter based on the outputs of at least one of said voice activity detector, said target-to-jammer ratio estimator, and said signal-to-noise ratio estimator.

16. A directional processing system as claimed in claim 15, wherein said transform domain is a frequency domain.

17. A directional signal processing system for beamforming a plurality of information signals, said directional signal processing system comprising:

a plurality of microphones;

an analog-to-digital convertor for converting said information signals from said microphones to a plurality of digital information signals;

an oversampled filterbank comprising at least one analysis filterbank for transforming said digital information signals in time domain into a plurality of channel signals in transform domain, and one synthesis filterbank;

a signal processor for processing the outputs of said analysis filterbank for beamforming said information signals, said synthesis filterbank transforming the outputs of said signal processor to a single digital information signal in time domain;

a post-filter provided between said signal processor and said synthesis filterbank;

a controller for controlling said post-filter;

a digital-to-analog convertor for converting said single digital information signal to an analog information signal; and at least one of any of the following:

a voice activity detector;

a target-to-jammer ratio estimator;

a signal-to-noise ratio estimator;

a combination matrix provided between said analog-to-digital convertor and said analysis filterbank for pre-processing of said information signals in time domain; and an active noise processor comprising a microphone and a loop filter, wherein said combination matrix is a FIR filter or an IIR filter, wherein said controller controls said post filter based on the outputs of at least one of said voice activity detector, said target-to-jammer ratio estimator, and said signal-to-noise ratio estimator.

18. A directional processing system as claimed in claim 17, wherein said transform domain is a frequency domain.

19. A directional signal processing system for beamforming a plurality of information signals, said directional signal processing system comprising:

a plurality of microphones;

an analog-to-digital convertor for converting said information signals from said microphones to a plurality of digital information signals;

an oversampled filterbank comprising at least one analysis filterbank for transforming said digital information signals in time domain into a plurality of channel signals in transform domain, and one synthesis filterbank;

a signal processor for processing the outputs of said analysis filterbank for beamforming said information signals, said synthesis filterbank transforming the outputs of said signal processor to a single digital information signal in time domain;

a post-filter provided between said signal processor and said synthesis filterbank;

a controller for controlling said post-filter; and a digital-to-analog convertor for converting said single digital information signal to an analog information signal, wherein said signal processor comprises:

at least one multiplier for multiplying the outputs of said analysis filterbank with at least one weight factor;

at least one summation circuit for summing the outputs of said multiplier; and an adaptive processor for adjusting said weight factor based on the output of at least one of a voice active detector, a target-to-jammer ratio estimator, and a signal-to-noise ratio estimator.

20. A directional processing system as claimed in claim 19, further comprises at least one of any of the following:

said voice activity detector;

said target-to-jammer ratio estimator;

said signal-to-noise ratio estimator;

a combination matrix provided between said analog-to-digital convertor and said analysis filterbank for pre-processing of said information signals in time domain; and an active noise processor comprising a microphone and a loop filter.

21. A directional processing system as claimed in claim 20, wherein said transform domain is a frequency domain.

* * * * *